United States Patent
Pugh et al.

(10) Patent No.: US 9,446,262 B2
(45) Date of Patent: Sep. 20, 2016

(54) APPARATUS AND METHOD FOR FORMATION OF AN ENERGIZED OPHTHALMIC DEVICE FOR LIGHT THERAPY

(75) Inventors: Randall B. Pugh, Jacksonville, FL (US); William Chester Neeley, Melbourne, FL (US); Robertson Towart, Cove (GB); Mario Jozef Joanna Peeters, Meerhout (BE); Wilhelmus Drinkenburg, Molenschot (NL); Aleksandar Miletic, Moscow (RU)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 1095 days.

(21) Appl. No.: 13/362,275

(22) Filed: Jan. 31, 2012

(65) Prior Publication Data

US 2012/0199995 A1     Aug. 9, 2012

Related U.S. Application Data

(60) Provisional application No. 61/439,535, filed on Feb. 4, 2011.

(51) Int. Cl.
| | |
|---|---|
| B29C 35/08 | (2006.01) |
| A61N 5/06 | (2006.01) |
| B29D 11/00 | (2006.01) |
| G02C 7/04 | (2006.01) |
| G02C 11/04 | (2006.01) |

(52) U.S. Cl.
CPC ....... *A61N 5/0618* (2013.01); *B29D 11/00807* (2013.01); *G02C 7/04* (2013.01); *G02C 11/04* (2013.01); *A61N 2005/0648* (2013.01); *A61N 2005/0652* (2013.01); *A61N 2005/0663* (2013.01)

(58) Field of Classification Search
CPC ................ B29C 35/08; A61N 5/0618; B29D 11/00807
USPC ....................................... 264/1.36
See application file for complete search history.

(56) References Cited

U.S. PATENT DOCUMENTS

| | | | |
|---|---|---|---|
| 3,621,838 A | 11/1971 | Harding et al. | |
| 2003/0069616 A1* | 4/2003 | Skene et al. | 607/88 |
| 2005/0072032 A1* | 4/2005 | McCollum et al. | 40/546 |
| 2006/0136018 A1 | 6/2006 | Lack et al. | |

(Continued)

FOREIGN PATENT DOCUMENTS

| | | |
|---|---|---|
| CN | 1076872 A | 10/1993 |
| DE | 102006005652 A1 | 9/2007 |

(Continued)

OTHER PUBLICATIONS

Chinese Office Action Dated Mar. 2, 2015 for Application Number: 201280007438.1(PCT/US2012/023663); Received from Agent Mar. 10, 2015.

(Continued)

*Primary Examiner* — Christina Johnson
*Assistant Examiner* — Xue Liu

(57) ABSTRACT

This invention discloses methods and apparatus for providing an ophthalmic lens with light source capable of providing specific bandwidths of light to an eye of a wearer. In some embodiments, an ophthalmic lens is cast molded from a silicone hydrogel and an energy source and light source encapsulated within the ophthalmic lens.

28 Claims, 10 Drawing Sheets

(56) References Cited

U.S. PATENT DOCUMENTS

| | | |
|---|---|---|
| 2007/0285385 A1 | 12/2007 | Albert et al. |
| 2010/0001926 A1 | 1/2010 | Amirparviz et al. |
| 2010/0078837 A1* | 4/2010 | Pugh et al. ............... 264/1.38 |
| 2010/0110372 A1 | 5/2010 | Pugh et al. |

FOREIGN PATENT DOCUMENTS

| | | |
|---|---|---|
| WO | WO 2004096364 | 11/2004 |
| WO | WO 2010033683 | 3/2010 |
| WO | WO 2010039610 | 4/2010 |
| WO | WO 2010051203 A1 * | 5/2010 |

OTHER PUBLICATIONS

International Search Report for PCT PCT/US2012/023663 Date of mailing Jul. 18, 2012.

* cited by examiner

```
┌─────────────────────────────────────────┐
│ PLACE THE ENERGY SOURCE AND LIGHT       │
│ SOURCE MOUNTED ON A MEDIA WITHIN A      │
│ MOLD CAVITY FOR FORMING AN              │
│ OPHTHALMIC LENS            501          │
└─────────────────────────────────────────┘
                    │
┌─────────────────────────────────────────┐
│ PLACE THE ENERGY SOURCE IN ELECTRICAL   │
│ COMMUNICATION WITH A LIGHT SOURCE OR    │
│ OTHER COMPONENT ADDITIONALLY            │
│ MOUNTED ON A MEDIA         502          │
└─────────────────────────────────────────┘
                    │
┌─────────────────────────────────────────┐
│ POLYMERIZE REACTIVE MIXTURE WITHIN THE  │
│ CAVITY TO FORM AN OPHTHALMIC LENS       │
│                            503          │
└─────────────────────────────────────────┘
```

FIG. 5

APPARATUS AND METHOD FOR FORMATION OF AN ENERGIZED OPHTHALMIC DEVICE FOR LIGHT THERAPY

RELATED APPLICATIONS

This application claims priority to U.S. Provisional Patent Application No. 61/439,535, filed Feb. 4, 2011; the contents of which are relied upon and incorporated by reference.

FIELD OF USE

This invention describes methods and apparatus for the fabrication of an energized biomedical device and, more specifically, in some embodiments, the fabrication of an energized ophthalmic lens for light therapy.

BACKGROUND

Seasonal affective disorder (SAD) is a well-established mood disorder wherein sufferers experience depressive symptoms in a certain season of the year, most frequently during winter months. Those affected by SAD often have normal mental health during most of the year. Symptoms of SAD may include, but are not limited to, excessive sleeping, lack of energy, craving carbohydrates, difficulty concentrating, and withdrawal from social activities. The symptoms result in feelings of depression, hopelessness, pessimism, and lack of pleasure.

Seasonal mood variations are believed to be related to changes in exposure to light. Geographic areas, such as the Arctic region, that experience fewer daylight hours, lower sunlight intensity, or significant periods of overcast skies exhibit a greater incidence of SAD. Variations in prevalence of SAD within the adult population are evident within the United States, ranging from low rates in Florida and other sunny states to notably higher rates in Alaska, New Hampshire and other northern or overcast areas.

Light therapy has been researched and established as a prominent and effective treatment for classic, or winter-based, seasonal affective disorder. Light therapy employs a device which emits significantly more lumens than a standard incandescent lamp. Common implementations include the preferred bright white full spectrum light at 10,000 lux, or optionally blue light at a wavelength of 480 nm at 2,500 lux, or green light at a wavelength of 500 nm at 350 lux. Light therapy normally requires a patient to sit with their eyes open at a prescribed distance from the light source for thirty to sixty minutes each day. This seasonal treatment is maintained for several weeks until the patient experiences frequent exposure to natural light. A majority of patients find the therapy inconvenient and a considerable percentage, in some studies up to 19%, therefore stop treatment. New methods and approaches are therefore desirable to deliver light therapy in a more convenient, continuous, and intelligent manner.

SUMMARY

Accordingly, the present invention includes methods and apparatus for forming a biomedical device, such as an ophthalmic lens, with an energized portion and a light source for delivering light therapy. Included are a disclosure of an energized ophthalmic lens with light sources, apparatus for forming an energized ophthalmic lens with light sources and methods for the same. An energy source, light source, and other desired components can be deposited onto one, or both of, a first mold part and a second mold part, or into an insert which is deposited onto one, or both of, a first mold part and a second mold part. A reactive monomer mix is placed between the first mold part and the second mold part. The first mold part is positioned proximate to the second mold part thereby forming a lens cavity with the energy source and light source and at least some of the reactive monomer mix in the lens cavity; and the reactive monomer mix is exposed to actinic radiation. Lenses are formed via the control of actinic radiation to which the reactive monomer mixture is exposed.

DESCRIPTION OF THE DRAWINGS

FIG. 5 illustrates method steps according to some additional aspect of the present invention.

DETAILED DESCRIPTION OF THE INVENTION

Figure 1:
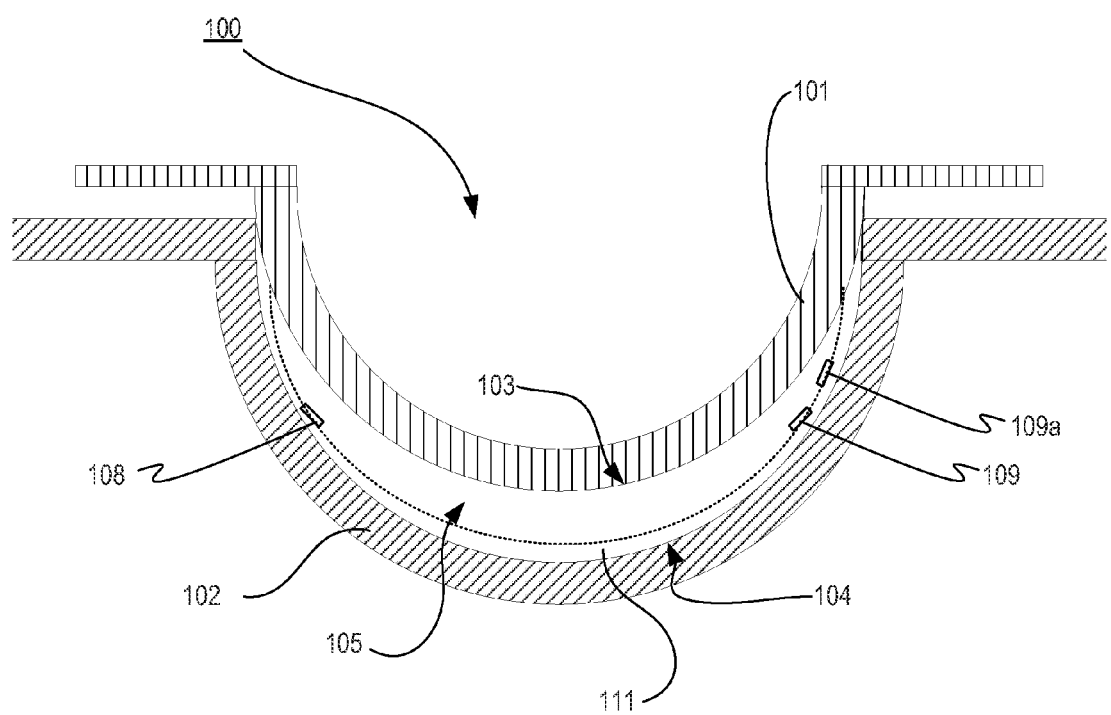
FIG. 1 illustrates a mold assembly apparatus according to some embodiments of the present invention.

The present invention includes methods and apparatus for forming biomedical devices, such as ophthalmic lenses. In particular, the present invention includes methods and apparatus for providing an ophthalmic lens with an Energy Source and Light Source incorporated into it. In some embodiments, the present invention includes a hydrogel contact lens including a generally annular area around a periphery of an optic zone in the contact lens with an energy source and component located within the annular area around the periphery.

In the following sections detailed descriptions of embodiments of the invention will be given. The description of both preferred and alternative embodiments are exemplary embodiments only, and it is understood that to those skilled in the art that variations, modifications and alterations may be apparent. It is therefore to be understood that said exemplary embodiments do not limit the scope of the underlying invention.

Glossary

In this description and claims directed to the presented invention, various terms may be used for which the following definitions will apply:

Component: as used herein refers to a device which draws electrical current from an Energy Source to perform one or more of a change of logical state or physical state.

Energized: as used herein refers to the state of being able to supply electrical current to or to have electrical energy stored within.

Energy: as used herein refers to the capacity of a physical system to do work. Many uses within this invention may relate to the said capacity being able to perform electrical actions in doing work.

Energy Source: as used herein refers to device capable of supplying Energy or placing a biomedical device in an Energized state.

Energy Harvesters: as used herein refers to device capable of extracting energy from the environment and convert it to electrical energy.

Intelligent light therapy: as used herein refers to a method of delivering light therapy whereby a processor evaluates various data and, based on data analysis, dynamically makes compensating adjustments to a programmed light therapy schedule. Adjusting light therapy based on the user's exposure to ambient light is one example of intelligent light therapy.

Lens: refers to any ophthalmic device that resides in or on the eye. These devices can provide optical correction or may be cosmetic. For example, the term lens can refer to a contact lens, intraocular lens, overlay lens, ocular insert, optical insert or other similar device through which vision is corrected or modified, or through which eye physiology is cosmetically enhanced (e.g. iris color) without impeding vision. In some embodiments, the preferred lenses of the invention are soft contact lenses made from silicone elastomers or hydrogels, which include but are not limited to silicone hydrogels, and fluorohydrogels.

Lens forming mixture or "Reactive Mixture" or "RMM" (reactive monomer mixture): as used herein refers to a monomer or prepolymer material which can be cured and crosslinked or crosslinked to form an ophthalmic lens. Various embodiments can include lens forming mixtures with one or more additives such as: UV blockers, tints, photoinitiators or catalysts, and other additives one might desire in an ophthalmic lenses such as, contact or intraocular lenses.

Lens Forming Surface: refers to a surface that is used to mold a lens. In some embodiments, any such surface 103-104 can have an optical quality surface finish, which indicates that it is sufficiently smooth and formed so that a lens surface fashioned by the polymerization of a lens forming material in contact with the molding surface is optically acceptable. Further, in some embodiments, the lens forming surface 103-104 can have a geometry that is necessary to impart to the lens surface the desired optical characteristics, including without limitation, spherical, aspherical and cylinder power, wave front aberration correction, corneal topography correction and the like as well as any combinations thereof.

Light Source: as used herein refers to a device capable of emitting light.

Light therapy: as used herein refers to exposure to specific wavelengths of light, controlled with various devices, and administered for a specified amount of time, at a specified intensity, and, in some cases, at a specified time of day.

Lithium Ion Cell: refers to an electrochemical cell where Lithium ions move through the cell to generate electrical energy. This electrochemical cell, typically called a battery, may be reenergized or recharged in its typical forms.

Lux: as used herein refers to units of illumination in the International System of Units (SI). Lux provides a measure of luminous power per area. One lux is the amount of illumination provided when one lumen is evenly distributed over an area of one square meter. This is also equivalent to the illumination that would exist on a surface all points of which are one meter from a point source of one international candle. One lux is equal to 0.0929 foot-candle.

Mold: refers to a rigid or semi-rigid object that may be used to form lenses from uncured formulations. Some preferred molds include two mold parts forming a front curve mold part and a back curve mold part.

Optical Zone: as used herein refers to an area of an ophthalmic lens through which a wearer of the ophthalmic lens sees.

Power: as used herein refers to work done or energy transferred per unit of time.

Programmed light therapy schedule: as used herein refers to a set of automated instructions that controls light therapy timing, duration and intensity based on variables such as dates, geographic region, and severity of a user's seasonal affective disorder symptoms. A programmed light therapy schedule may be set by an eye care professional, a medical doctor, or a user.

Rechargeable or Re-energizable: as used herein refers to a capability of being restored to a state with higher capacity to do work. Many uses within this invention may relate to the capability of being restored with the ability to flow electrical current at a certain rate for a certain, reestablished time period.

Reenergize or Recharge: To restore to a state with higher capacity to do work. Many uses within this invention may relate to restoring a device to the capability to flow electrical current at a certain rate for a certain, reestablished time period.

Released from a mold: means that a lens is either completely separated from the mold, or is only loosely attached so that it can be removed with mild agitation or pushed off with a swab.

Seasonal Affective Disorder (SAD): as used herein refers to a mood disorder that occurs during seasons when exposure to sunlight is limited, characterized by symptoms of depression and relieved by the arrival of spring or by light therapy. A recurrent state of depression, usually experienced by people in winter, thought to be related to lack of sunlight.

An energized lens 100 with an embedded Energy Source 109 may include an electrochemical cell or battery as the storage means for the energy and in some embodiments, encapsulation and isolation of the materials comprising the Energy Source from an environment into which an ophthalmic lens is placed.

In some embodiments, a pattern of circuitry and Energy Sources 109 can be located exterior to an optic zone through which a wearer of a lens would see, while other embodiments can include a pattern of conductive material which is small enough to not adversely affect the sight of a contact lens wearer and therefore can be located within, or exterior to, an optical zone.

In general, according to some embodiments of the present invention, an Energy Source is embodied within an ophthalmic lens via automation which places an Energy Source 109 a desired location relative to a mold part used to fashion the lens.

In some embodiments, an Energy Source 109 is placed in electrical communication with a component which can be activated on command and draws electrical current from the Energy Source 109 included within the ophthalmic lens. A component 108 can include for example, a semiconductor device, an active or passive electrical device or an electrically activated machine, including for example: Microelectromechanical systems (MEMS), nanoelectromechanical systems (NEMS), or micromachines. A semiconductor, or active or passive electrical device may include, in some embodiments, a display that is perceptible to the human eye. Subsequent to placing the Energy Source and component, a Reactive Mixture can be shaped by the mold part and polymerized to form the ophthalmic lens.

Molds

Referring now to FIG. 1, a diagram of an exemplary mold 100 for an ophthalmic lens is illustrated with an Energy Source 109 and a Light Source 109a. As used herein, the term mold includes a single or multi-part device 100 having a cavity 105 into which a lens forming mixture can be dispensed such that upon reaction or cure of the lens forming mixture, an ophthalmic lens of a desired shape is produced. The molds and mold assemblies 100 of this invention are made up of more than one "mold parts" or "mold pieces" 101-102. The mold parts 101-102 can be brought together such that a cavity 105 is formed between the mold parts 101-102 in which a lens can be formed. This combination of mold parts 101-102 is preferably temporary. Upon formation of the lens, the mold parts 101-102 can again be separated for removal of the lens.

At least one mold part 101-102 has at least a portion of its surface 103-104 in contact with the lens forming mixture such that upon reaction or cure of the lens forming mixture that surface 103-104 provides a desired shape and form to the portion of the lens with which it is in contact. The same is true of at least one other mold part 101-102.

Thus, for example, in a preferred embodiment a mold assembly 100 is formed from two parts 101-102, a female concave piece (front piece) 102 and a male convex piece (back piece) 101 with a cavity formed between them. The portion of the concave surface 104 which makes contact with lens forming mixture has the curvature of the front curve of an ophthalmic lens to be produced in the mold assembly 100 and is sufficiently smooth and formed such that the surface of an ophthalmic lens formed by polymerization of the lens forming mixture which is in contact with the concave surface 104 is optically acceptable.

In some embodiments, the front mold piece 102 can also have an annular flange integral with and surrounding circular circumferential edge and extends from it in a plane normal to the axis and extending from the flange (not shown).

A lens forming surface can include a surface 103-104 with an optical quality surface finish, which indicates that it is sufficiently smooth and formed so that a lens surface fashioned by the polymerization of a lens forming material in contact with the molding surface is optically acceptable. Further, in some embodiments, the lens forming surface 103-104 can have a geometry that is necessary to impart to the lens surface the desired optical characteristics, including without limitation, spherical, aspherical and cylinder power, wave front aberration correction, corneal topography correction and the like as well as any combinations thereof.

At 111, a media is illustrated onto which an Energy Source 109 and a Light Source 109a may be placed. The media 111 may be any receiving material onto which an Energy Source 109 and a Light Source 109a may be placed, in some embodiments may also include circuit paths, Components 108 and other aspects useful to use of the energy source. In some embodiments, the media 111 can be a clear coat of a material which may be incorporated into a lens when the lens is formed. The clear coat can include for example a pigment as described below, a monomer or other biocompatible material. Additional embodiments can include a media comprising an insert, which can be either rigid or formable. In some embodiments, a rigid insert may include an optical zone providing an optical property (such as those utilized for vision correction) and a non-optical zone portion. An Energy Source 109 can be placed on one or both of the optic zone and non-optic zone of the insert. Still other embodiments can include an annular insert, either rigid or formable or some shape which circumvents an optic zone through which a user sees.

Various embodiments also include placing an Energy Source 109 and a Light Source 109a onto an insert prior to placement of the insert into a mold portion used to form a lens. A media 111 may also include an insert with one or more Components 108 which will receive an electrical charge via the Energy Source 109.

Mold part 101-102 material can include, for example: a polyolefin of one or more of: polypropylene, polystyrene, polyethylene, polymethyl methacrylate, and modified polyolefins. Other molds can include a ceramic or metallic material.

A preferred alicyclic co-polymer contains two different alicyclic polymers and is sold by Zeon Chemicals L.P. under the trade name ZEONOR. There are several different grades of ZEONOR. Various grades may have glass transition temperatures ranging from 105° C. to 160° C. A specifically preferred material is ZEONOR1060R.

Other mold materials that may be combined with one or more additives to form an ophthalmic lens mold include, for example, Zieglar-Natta polypropylene resins (sometimes referred to as znPP).

Still further, in some embodiments, the molds of the invention may contain polymers such as polypropylene, polyethylene, polystyrene, polymethyl methacrylate, modified polyolefins containing an alicyclic moiety in the main chain and cyclic polyolefins. This blend can be used on either or both mold halves, where it is preferred that this blend is used on the back curve and the front curve consists of the alicyclic co-polymers.

In some preferred methods of making molds 100 according to the present invention, injection molding is utilized according to known techniques, however, embodiments can also include molds fashioned by other techniques including, for example: free form molding, lathing, diamond turning, or laser cutting.

Typically, lenses are formed on at least one surface of both mold parts 101-102. However, in some embodiments, one surface of a lens may be formed from a mold part 101-102 and another surface of a lens can be formed using a lathing method, or other methods.

Lenses

Figure 2:
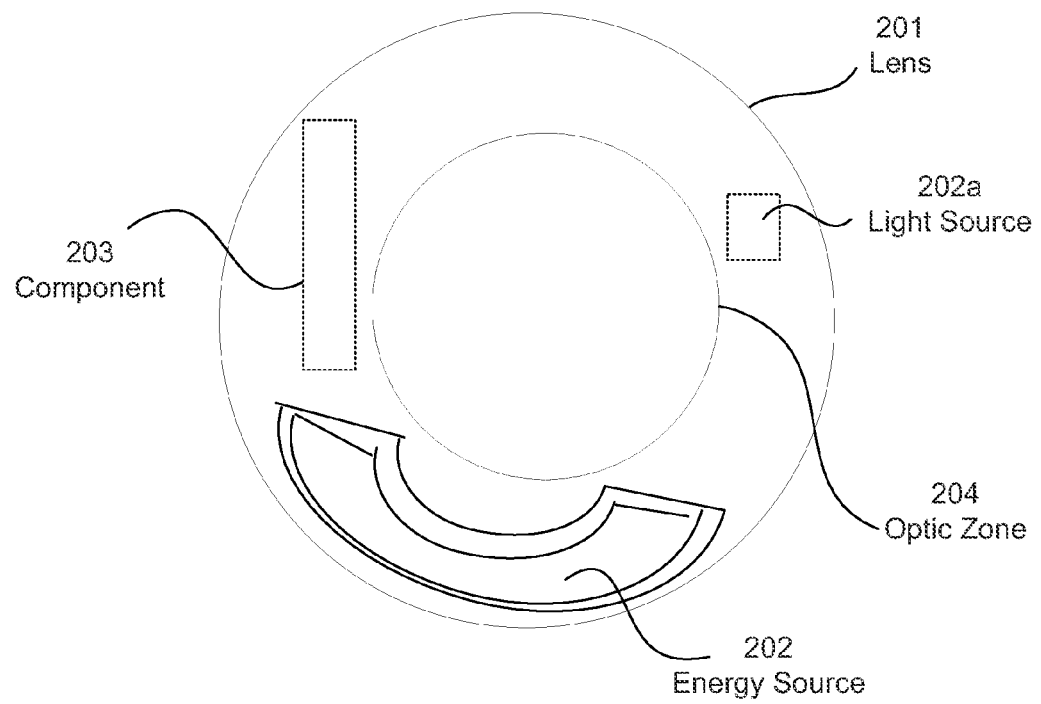
FIG. 2 illustrates an ophthalmic lens with an Energy Source and component included.

Referring now to FIG. 2, an ophthalmic lens 201 is illustrated with an Energy Source 202, a Light Source 202a, and a Component 203.

The Energy Source 202 can be in electrical communication with a Light Source 202a and a Component 203. The Light Source 202a can include light-emitting diodes (LEDs) or other lights which emit blue light at wavelengths of 450 to 500 nanometers, most preferably at 470 to 480 nanometers, and at 2,000 to 3,000 lux. Alternatively, LEDs or other lights may emit green light at wavelengths of 475 to 525 nanometers, most preferably at 490 to 510 nanometers, and at 300 to 400 lux. In another embodiment, a single Light Source may be piped to one or more locations in an ophthalmic lens 201 to provide illumination required for light therapy. The component 203 can include any device which responds to an electrical charge with a change in state, such as, for example: a semiconductor type chip; a passive electrical device; an optical device such as a crystal lens; a processor, a micro-electromechanical machine (MEMS), or a nano-electromechanical machine (NEMS).

In some specific embodiments, the Component 203 includes an electrical storage device, such as, for example, a capacitor; ultracapacitor; supercapacitor; or other storage component. An Energy Source 202 can include, for example: a lithium ion battery located in the periphery of an ophthalmic lens outside of the optic zone and be chargeable via one or more of radio frequency; photo voltaics, and magnetic inductance into an Energy Source 202. Other Energy Sources 202 are further discussed with reference to FIG. 7 below.

As illustrated, in some embodiments, the Energy Source portion 202, the Light Source 202a, and the Component 203 are located outside of an optic zone 204, wherein the optic zone 204 includes that portion of the lens 201 providing line of sight for a wearer of the lens 201. Other embodiments may include an Energy Source 202 in the optic zone portion of an ophthalmic lens. For example, such embodiments can include an Energy Source 202 of conductive particles too small to be viewable without aid to the human eye.

In some embodiments, a preferred lens type can include a lens 201 that includes a silicone containing component. A "silicone-containing component" is one that contains at least one [—Si—O—] unit in a monomer, macromer or prepolymer. Preferably, the total Si and attached O are present in the silicone-containing component in an amount greater than about 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, vinyl, N-vinyl lactam, N-vinylamide, and styryl functional groups.

Suitable silicone containing components include compounds of Formula I

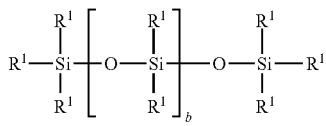

where
$R^1$ is independently selected from monovalent reactive groups, monovalent alkyl groups, or monovalent aryl groups, any of the foregoing which may further comprise functionality selected from hydroxy, amino, oxa, carboxy, alkyl carboxy, alkoxy, amido, carbamate, carbonate, halogen or combinations thereof; and monovalent siloxane chains comprising 1-100 Si—O repeat units which may further comprise functionality selected from alkyl, hydroxy, amino, oxa, carboxy, alkyl carboxy, alkoxy, amido, carbamate, halogen or combinations thereof;

where b=0 to 500, where it is understood that when b is other than 0, b is a distribution having a mode equal to a stated value;

wherein at least one $R^1$ comprises a monovalent reactive group, and in some embodiments between one and 3 $R^1$ comprise monovalent reactive groups.

As used herein "monovalent reactive groups" are groups that can undergo free radical and/or cationic polymerization. Non-limiting examples of free radical reactive groups include (meth)acrylates, styryls, vinyls, vinyl ethers, $C_{1-6}$alkyl(meth)acrylates, (meth)acrylamides, $C_{1-6}$alkyl(meth)acrylamides, N-vinyllactams, N-vinylamides, $C_{2-12}$alkenyls, $C_{2-12}$alkenylphenyls, $C_{2-12}$alkenylnaphthyls, $C_{2-6}$alkenylphenyl$C_{1-6}$alkyls, O-vinylcarbamates and O-vinylcarbonates. Non-limiting examples of cationic reactive groups include vinyl ethers or epoxide groups and mixtures thereof. In one embodiment the free radical reactive groups comprises (meth)acrylate, acryloxy, (meth)acrylamide, and mixtures thereof.

Suitable monovalent alkyl and aryl groups include unsubstituted monovalent $C_1$ to $C_{16}$alkyl groups, $C_6$-$C_{14}$ aryl groups, such as substituted and unsubstituted methyl, ethyl, propyl, butyl, 2-hydroxypropyl, propoxypropyl, polyethyleneoxypropyl, combinations thereof and the like.

In one embodiment b is zero, one $R^1$ is a monovalent reactive group, and at least 3 $R^1$ are selected from monovalent alkyl groups having one to 16 carbon atoms, and in another embodiment from monovalent alkyl groups having one to 6 carbon atoms. Non-limiting examples of silicone components of this embodiment include 2-methyl-, 2-hydroxy-3-[3-[1,3,3,3-tetramethyl-1-[(trimethylsilyl)oxy]disiloxanyl]propoxy]propyl ester ("SiGMA"), 2-hydroxy-3-methacryloxypropyloxypropyl-tris(trimethylsiloxy)silane, 3-methacryloxypropyltris(trimethylsiloxy)silane ("TRIS"), 3-methacryloxypropylbis(trimethylsiloxy)methylsilane and 3-methacryloxypropylpentamethyl disiloxane.

In another embodiment, b is 2 to 20, 3 to 15 or in some embodiments 3 to 10; at least one terminal $R^1$ comprises a monovalent reactive group and the remaining $R^1$ are selected from monovalent alkyl groups having 1 to 16 carbon atoms, and in another embodiment from monovalent alkyl groups having 1 to 6 carbon atoms. In yet another embodiment, b is 3 to 15, one terminal $R^1$ comprises a monovalent reactive group, the other terminal $R^1$ comprises a monovalent alkyl group having 1 to 6 carbon atoms and the remaining $R^1$ comprise monovalent alkyl group having 1 to 3 carbon atoms. Non-limiting examples of silicone components of this embodiment include (mono-(2-hydroxy-3-methacryloxypropyl)-propyl ether terminated polydimethylsiloxane (400-1000 MW)) ("OH-mPDMS"), monomethacryloxypropyl terminated mono-n-butyl terminated polydimethylsiloxanes (800-1000 MW), ("mPDMS").

In another embodiment b is 5 to 400 or from 10 to 300, both terminal $R^1$ comprise monovalent reactive groups and the remaining $R^1$ are independently selected from monovalent alkyl groups having 1 to 18 carbon atoms which may have ether linkages between carbon atoms and may further comprise halogen.

In one embodiment, where a silicone hydrogel lens is desired, the lens of the present invention will be made from a reactive mixture comprising at least about 20 and preferably between about 20 and 70% wt silicone containing components based on total weight of reactive monomer components from which the polymer is made.

In another embodiment, one to four $R^1$ comprises a vinyl carbonate or carbamate of the formula:

Formula II
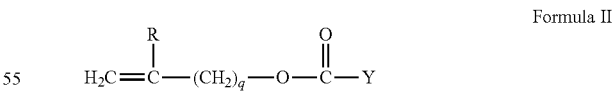

wherein: Y denotes O—, S— or NH—;
R denotes, hydrogen or methyl; d is 1, 2, 3 or 4; and q is 0 or 1.

The silicone-containing vinyl carbonate or vinyl carbamate monomers specifically include: 1,3-bis[4-(vinyloxycarbonyloxy)but-1-yl]tetramethyl-disiloxane; 3-(vinyloxycarbonylthio) propyl-[tris(trimethylsiloxy)silane]; 3-[tris(trimethylsiloxy)silyl]propyl allyl carbamate; 3-[tris(trimethylsiloxy)silyl]propyl vinyl carbamate; trimethylsilylethyl vinyl carbonate; trimethylsilylmethyl vinyl carbonate, and

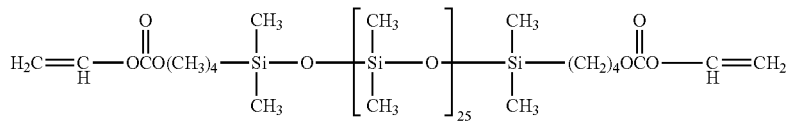

Where biomedical devices with modulus below about 200 are desired, only one $R^1$ shall comprise a monovalent reactive group and no more than two of the remaining $R^1$ groups will comprise monovalent siloxane groups.

Another class of silicone-containing components includes polyurethane macromers of the following formulae:

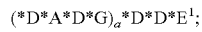

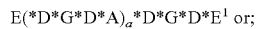

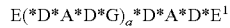                          Formulae IV-VI wherein:

D denotes an alkyl diradical, an alkyl cycloalkyl diradical, a cycloalkyl diradical, an aryl diradical or an alkylaryl diradical having 6 to 30 carbon atoms, G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

* denotes a urethane or ureido linkage;

$a$ is at least 1;

A denotes a divalent polymeric radical of formula:

Formula VII

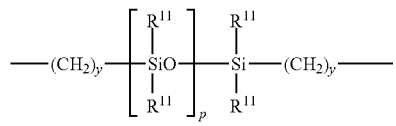

$R^{11}$ independently denotes an alkyl or fluoro-substituted alkyl group having 1 to 10 carbon atoms which may contain ether linkages between carbon atoms; y is at least 1; and p provides a moiety weight of 400 to 10,000; each of E and $E^1$ independently denotes a polymerizable unsaturated organic radical represented by formula:

Formula VIII

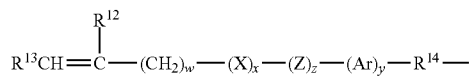

wherein: $R^{12}$ is hydrogen or methyl; $R^{13}$ is hydrogen, an alkyl radical having 1 to 6 carbon atoms, or a —CO—Y—$R^{15}$ radical wherein Y is —O—, Y—S— or —NH—; $R^{14}$ is a divalent radical having 1 to 12 carbon atoms; X denotes —CO— or —OCO—; Z denotes —O— or —NH—; Ar denotes an aromatic radical having 6 to 30 carbon atoms; w is 0 to 6; x is 0 or 1; y is 0 or 1; and z is 0 or 1.

A preferred silicone-containing component is a polyurethane macromer represented by the following formula:

Formula IX

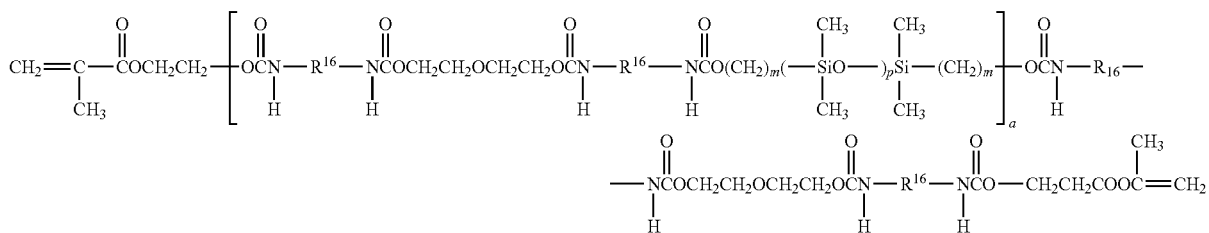

wherein $R^{16}$ is a diradical of a diisocyanate after removal of the isocyanate group, such as the diradical of isophorone diisocyanate. Another suitable silicone containing macromer is compound of formula X (in which x+y is a number in the range of 10 to 30) formed by the reaction of fluoroether, hydroxy-terminated polydimethylsiloxane, isophorone diisocyanate and isocyanatoethylmethacrylate.

Formula X

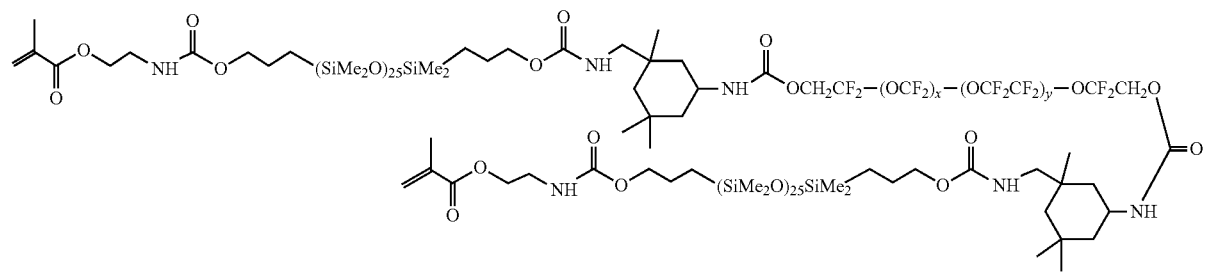

Other silicone containing components suitable for use in this invention include macromers containing polysiloxane, polyalkylene ether, diisocyanate, polyfluorinated hydrocarbon, polyfluorinated ether and polysaccharide groups; polysiloxanes with a polar fluorinated graft or side group having a hydrogen atom attached to a terminal difluoro-substituted carbon atom; hydrophilic siloxanyl methacrylates containing ether and siloxanyl linkanges and crosslinkable monomers containing polyether and polysiloxanyl groups. Any of the foregoing polysiloxanes can also be used as the silicone containing component in this invention.

Processes

The following method steps are provided as examples of processes that may be implemented according to some aspects of the present invention. It should be understood that the order in which the method steps are presented is not meant to be limiting and other orders may be used to implement the invention. In addition, not all of the steps are required to implement the present invention and additional steps may be included in various embodiments of the present invention.

Figure 4:
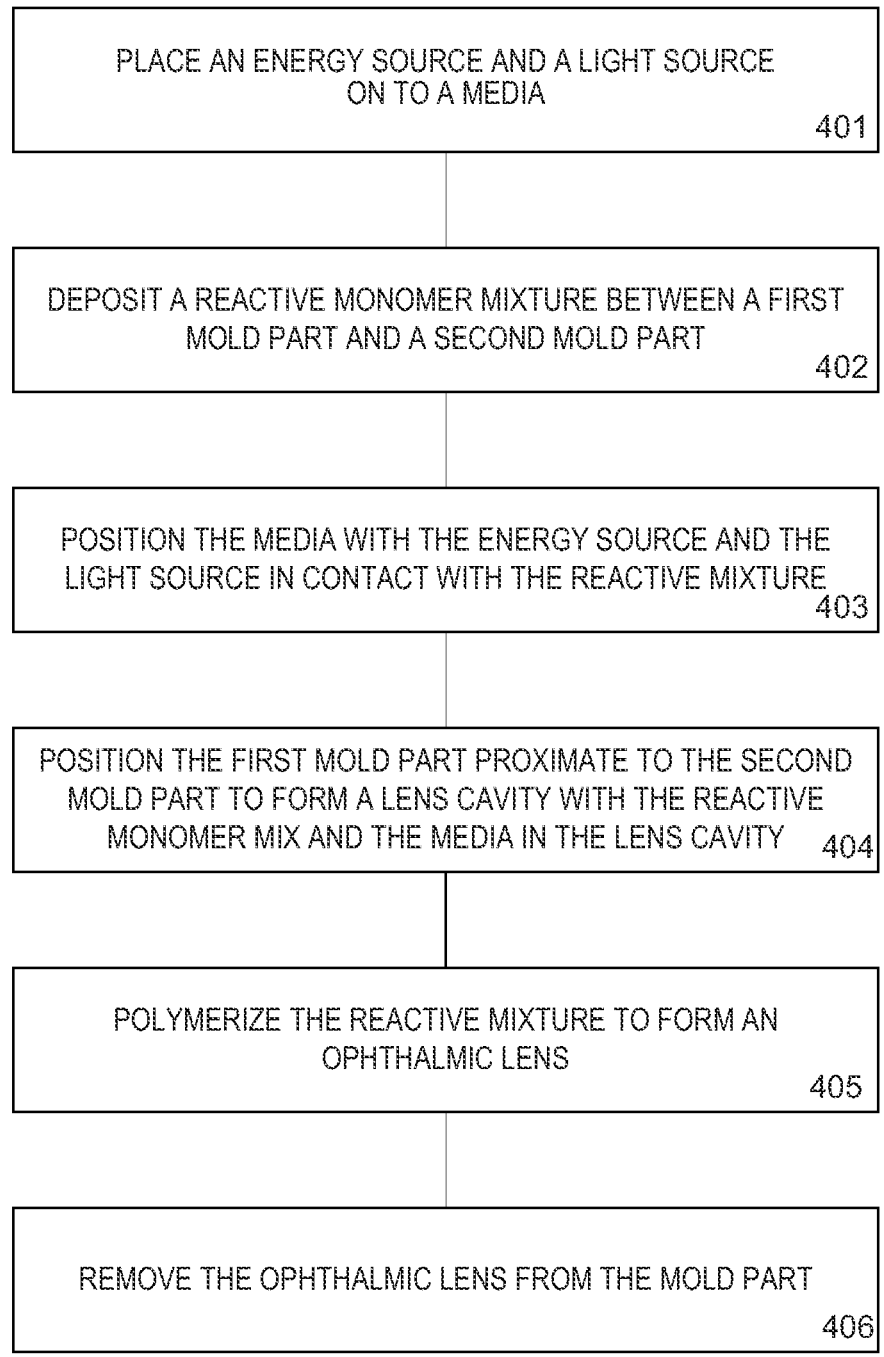
FIG. 4 illustrates method steps according to some embodiments of the present invention.

Referring now to FIG. 4, a flowchart illustrates exemplary steps that may be used to implement the present invention, at 401, an Energy Source and a Light Source are placed on to a media. The media may or may not also contain one or more components.

At 402, a reactive monomer mix can be deposited into a mold part 101-102.

At 403, the media is placed into the mold part. In some preferred embodiments, the media is placed in the mold part via mechanical placement. Mechanical placement can include, for example, a robot or other automation, such as those known in the industry to place surface mount components. Human placement of a media is also within the scope of the present invention. Accordingly, any mechanical placement effective to place a media with an Energy Source and a Light Source within a cast mold part such that the polymerization of a Reactive Mixture contained by the mold part will include the Energy Source and the Light Source in a resultant ophthalmic lens.

In some embodiments, a binder layer can be applied to a mold part prior to placement of the Energy Source and the Light Source on the mold part. A binder layer can include, by way of non-limiting example, a pigment or a monomer. The binding layer may be applied for example via an ink jetting or pad printing process. In some embodiments, a processor device, MEMS, NEMS or other component may also be placed into the binder in electrical contact with the Energy Source.

At 404, the first mold part can be placed proximate to the second mold part to form a lens forming cavity with at least some of the reactive monomer mix, the Energy Source and the Light Source in the cavity. At 405, the reactive monomer mix within the cavity can be polymerized. Polymerization can be accomplished for example via exposure to one or both of actinic radiation and heat. At 406, the lens is removed from the mold parts.

In some embodiments, a binding layer can include a binding polymer that is capable of forming an interpenetrating polymer network with a lens material, eliminating the need for formation of covalent bonds between the binder and lens material to form a stable lens. Stability of a lens with an Energy Source and a Light Source placed into the binder is provided by entrapment of the Energy Source and the Light Source in the binding polymer and the lens base polymer. The binding polymers of the invention can include, for example, those made from a homopolymer or copolymer, or combinations thereof, having similar solubility parameters to each other and the binding polymer has similar solubility parameters to the lens material. Binding polymers may contain functional groups that render the polymers and copolymers of the binding polymer capable of interactions with each other. The functional groups can include groups of one polymer or copolymer interacting with that of another in a manner that increases the density of the interactions helping to inhibit the mobility of and/or entrap the pigment particles. The interactions between the functional groups may be polar, dispersive, or of a charge transfer complex nature. The functional groups may be located on the polymer or copolymer backbones or be pendant from the backbones.

By way of non-limiting example, a monomer, or mixture of monomers, that form a polymer with a positive charge may be used in conjunction with a monomer or monomers that form a polymer with a negative charge to form the binding polymer.

As a more specific example, methacrylic acid ("MAA") and 2-hydroxyethylmethacrylate ("HEMA") may be used to provide a MAA/HEMA copolymer that is then mixed with a HEMA/3-(N,N-dimethyl) propyl acrylamide copolymer to form the binding polymer.

As another example, the binding polymer may be composed of hydrophobically-modified monomers including, without limitation, amides and esters of the formula:

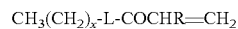

wherein L may be —NH or oxygen, x may be a whole number from 2 to 24, R may be a $C_1$ to $C_6$ alkyl or hydrogen and preferably is methyl or hydrogen. Examples of such amides and esters include, without limitation, lauryl methacrylamide, and hexyl methacrylate. As yet another example, polymers of aliphatic chain extended carbamates and ureas may be used to form the binding polymer.

Binding polymers suitable for a binding layer 111 may also include a random block copolymer of HEMA, MAA and lauryl methacrylate ("LMA"), a random block copolymer of HEMA and MAA or HEMA and LMA, or a homopolymer of HEMA.

The weight percentages, based on the total weight of the binding polymer, of each component in these embodiments is about 93 to about 100 weight percent HEMA, about 0 to about 2 weight percent MAA, and about 0 to about 5 weight percent LMA.

The molecular weight of the binding polymer can be such that it is somewhat soluble in the lens material and swells in it. The lens material diffuses into the binding polymer and is polymerized and/or cross-linked. However, at the same time, the molecular weight of the binding polymer cannot be so high as to impact the quality of the printed image. Preferably, the molecular weight of the binding polymer is about 7,000 to about 100,000, more preferably about 7,000 to about 40,000, most preferably about 17,000 to about 35,000 $M_{peak}$ which corresponds to the molecular weight of the highest peak in the SEC analyses ($=(M_n \times M_w)^{1/2}$)

For purposes of the invention, the molecular weight can be determined using a gel permeation chromatograph with a 90° light scattering and refractive index detectors. Two columns of PW4000 and PW2500, a methanol-water eluent of 75/25 wt/wt adjusted to 50 mM sodium chloride and a mixture of polyethylene glycol and polyethylene oxide molecules with well defined molecular weights ranging from 325,000 to 194 are used.

One ordinarily skilled in the art will recognize that, by using chain transfer agents in the production of the binding polymer, by using large amounts of initiator, by using living polymerization, by selection of appropriate monomer and initiator concentrations, by selection of amounts and types of solvent, or combinations thereof, the desired binding polymer molecular weight may be obtained. Preferably, a chain transfer agent is used in conjunction with an initiator, or more preferably with an initiator and one or more solvents to achieve the desired molecular weight. Alternatively, small amounts of very high molecular weight binding polymer may be used in conjunction with large amounts of solvent to maintain a desired viscosity for the binding polymer. Preferably, the viscosity of the binding polymer will be about 4,000 to about 15,000 centipoise at 23° C.

Chain transfer agents useful in forming the binding polymers used in the invention have chain transfer constants values of greater than about 0.01, preferably greater than about 7, and more preferably greater than about 25,000.

Any desirable initiators may be used including, without limitation, ultra-violet, visible light, thermal initiators and the like and combinations thereof. Preferably, a thermal initiator is used, more preferably 2,2-azobis isobutyronitrile and 2,2-azobis 2-methylbutyronitrile. The amount of initiator used will be about 0.1 to about 5 weight percent based on the total weight of the formulation. Preferably, 2,2-azobis 2-methylbutyronitrile is used with dodecanethiol.

A binding polymer layer or other media 111 may be made by any convenient polymerization process including, without limitation, radical chain polymerization, step polymerization, emulsion polymerization, ionic chain polymerization, ring opening, group transfer polymerization, atom transfer polymerization, and the like. Preferably, a thermal-initiated, free-radical polymerization is used. Conditions for carrying out the polymerization are within the knowledge of one ordinarily skilled in the art.

Solvents useful in the production of the binding polymer are medium boiling solvents having boiling points between about 120 and 230° C. Selection of the solvent to be used will be based on the type of binding polymer to be produced and its molecular weight. Suitable solvents include, without limitation, diacetone alcohol, cyclohexanone, isopropyl lactate, 3-methoxy 1-butanol, 1-ethoxy-2-propanol, and the like.

In some embodiments, a binding polymer layer of the invention may be tailored, in terms of expansion factor in water, to the lens material with which it will be used. Matching, or substantially matching, the expansion factor of the binding polymer with that of the cured lens material in packing solution may facilitate the avoidance of development of stresses within the lens that result in poor optics and lens parameter shifts. Additionally, the binding polymer can be swellable in the lens material, permitting swelling of the image printed using the colorant of the invention. Due to this swelling, the image becomes entrapped within the lens material without any impact on lens comfort.

In some embodiments, colorants may be included in the binding layer. Pigments useful with the binding polymer in the colorants of the invention are those organic or inorganic pigments suitable for use in contact lenses, or combinations of such pigments. The opacity may be controlled by varying the concentration of the pigment and opacifying agent used, with higher amounts yielding greater opacity. Illustrative organic pigments include, without limitation, pthalocyanine blue, pthalocyanine green, carbazole violet, vat orange #1, and the like and combinations thereof. Examples of useful inorganic pigments include, without limitation, iron oxide black, iron oxide brown, iron oxide yellow, iron oxide red, titanium dioxide, and the like, and combinations thereof. In addition to these pigments, soluble and non-soluble dyes may be used including, without limitation, dichlorotriazine and vinyl sulfone-based dyes. Useful dyes and pigments are commercially available.

Coating, or wetting, of the pigment particles with binding polymer provides better dispersion of the pigment particles in the bulk binding polymer. The coating may be achieved by use of electrostatic, dispersive, or hydrogen bonding forces to cover the pigment's surface. Preferably, a high shear force is used to disperse the pigment into the binding polymer. The pigment may be added to the binding polymer by dispensing the polymer and pigment into a suitable mixer, such as a rotary shaft mixer and mixing until a homogeneous mixture results, typically for a period of up to about 30 minutes. The mixture may be then fed into a high shear mill, such as an Eiger mill to disperse the pigment into the binding polymer. Repeated milling is carried out as necessary to achieve complete dispersion. Generally, milling is carried out until the pigments are about 0.2 to about 3 microns in size. Milling may be carried out using any suitable, commercially available device including, without limitation, a high shear or ball milling device.

In addition to the pigment and binding polymer, in some embodiments, the binding layer contains one or more solvents that aid in coating of the binding layer onto the mold part. It is another discovery of the invention that, to facilitate a binding layer that does not bleed or run on the mold part surface to which it is applied, it is desirable, and preferred, that the binding layer have a surface tension below about 27 mN/m. This surface tension may be achieved by treatment of the surface, for example a mold surface, to which the binding layer 111 will be applied. Surface treatments may be effected by methods known in the art, such as, but not limited to plasma and corona treatments. Alternatively, and preferably, the desired surface tension may be achieved by the choice of solvents used in the colorant.

Accordingly, exemplary solvents useful in the binding layer include those solvents that are capable of increasing or decreasing the viscosity of the binding layer and aiding in controlling the surface tension. Suitable solvents include, without limitation, cyclopentanones, 4-methyl-2-pentanone, 1-methoxy-2-propanol, 1-ethoxy-2-propanol, isopropyl lactate and the like and combinations thereof. Preferably, 1-ethoxy-2-propanol and isopropyl lactate are used.

In some preferred embodiments, at least three different solvents are used in the binding layer material of the invention. The first two of these solvents, both medium boiling point solvents, are used in the production of the binding polymer. Although these solvents may be stripped from the binding polymer after its formation, it is preferred that they are retained. Preferably, the two solvents are 1-ethoxy-2-propanol and isopropyl lactate. An additional low boiling solvent, meaning a solvent the boiling point of which is between about 75 and about 120° C., can be used to decrease the viscosity of the colorant as desired. Suitable low boiling solvents include, without limitation, 2-propanol, 1-methoxy-2-propanol, 1-propanol, and the like and combinations thereof. Preferably, 1-propanol is used.

The specific amount of solvents used can depend on a number of factors. For example, the amount of solvents used in forming the binding polymer will depend upon the molecular weight of the binding polymer desired and the constituents, such as the monomers and copolymers, used in the binding polymer. The amount of low boiling solvent used will depend upon the viscosity and surface tension desired for the colorant. Further, if the colorant is to be applied to a mold and cured with a lens material, the amount of solvent used will depend upon the lens and mold materials used and whether the mold material has undergone any surface treatment to increase its wettability. Determination of the precise amount of solvent to be used is within the skill of one ordinarily skilled in the art. Generally, the total weight of the solvents used will be about 40 to about 75 weight percent of solvent will be used.

In addition to the solvents, a plasticizer may be and, preferably is, added to the binding layer to reduce cracking during the drying of the binding layer and to enhance the diffusion and swelling of the binding layer by the lens material. The type and amount of plasticizer used will depend on the molecular weight of the binding polymer used and, for colorants placed onto molds that are stored prior to use, the shelf-life stability desired. Useful plasticizers include, without limitation, glycerol, propylene glycol, dipropylene glycol, tripropylene glycol, polyethylene glycol 200, 400, or 600, and the like and combinations thereof. Preferably, glycerol is used. Amounts of plasticizer used generally will be 0 to about 10 weight percent based on the weight of the colorant.

One ordinarily skilled in the art will recognize that additives other than those discussed also may be included in the binding layer composition of the invention. Suitable additives include, without limitation, additives that aid flow and leveling, additives for foam prevention, additives for rheology modification, and the like, and combinations thereof.

In some embodiments of the present invention, the binding layer becomes embedded in the lens material upon curing of the lens material. Thus, the binding layer may embed closer to the front or back surface of the lens formed depending on the surface of the mold to which the lens the binding layer is applied. Additionally, one or more layers of binding layer may be applied in any order. Although invention may be used to provide hard or soft contact lenses made of any known lens material, or material suitable for manufacturing such lenses, preferably, the lenses of the invention are soft contact lenses having water contents of about 0 to about 90 percent. More preferably, the lenses are made of monomers containing hydroxy groups, carboxyl groups, or both or be made from silicone-containing polymers, such as siloxanes, hydrogels, silicone hydrogels, and combinations thereof. Material useful for forming the lenses of the invention may be made by reacting blends of macromers, monomers, and combinations thereof along with additives such as polymerization initiators. Suitable materials include, without limitation, silicone hydrogels made from silicone macromers and hydrophilic monomers.

Referring now to FIG. 5, in another aspect of the present invention, an Energy Source and a Light Source mounted on a media is placed within a mold cavity for forming an ophthalmic lens. At 501, an Energy Source and a Light Source is placed within an ophthalmic lens mold part, as discussed above.

At 502, the Energy Source is placed in electrical communication with a Light Source or other component additionally mounted on the media and placed within the mold part. Electrical communication can be accomplished, for example, via circuitry incorporated into an insert, or via pathways ink jetted or otherwise formed directly upon lens material.

At 503, reactive mixture placed within a cavity is polymerized to form a lens. Polymerization can be accomplished, for example, by exposure of the reactive mixture to actinic radiation.

Apparatus

Figure 3:
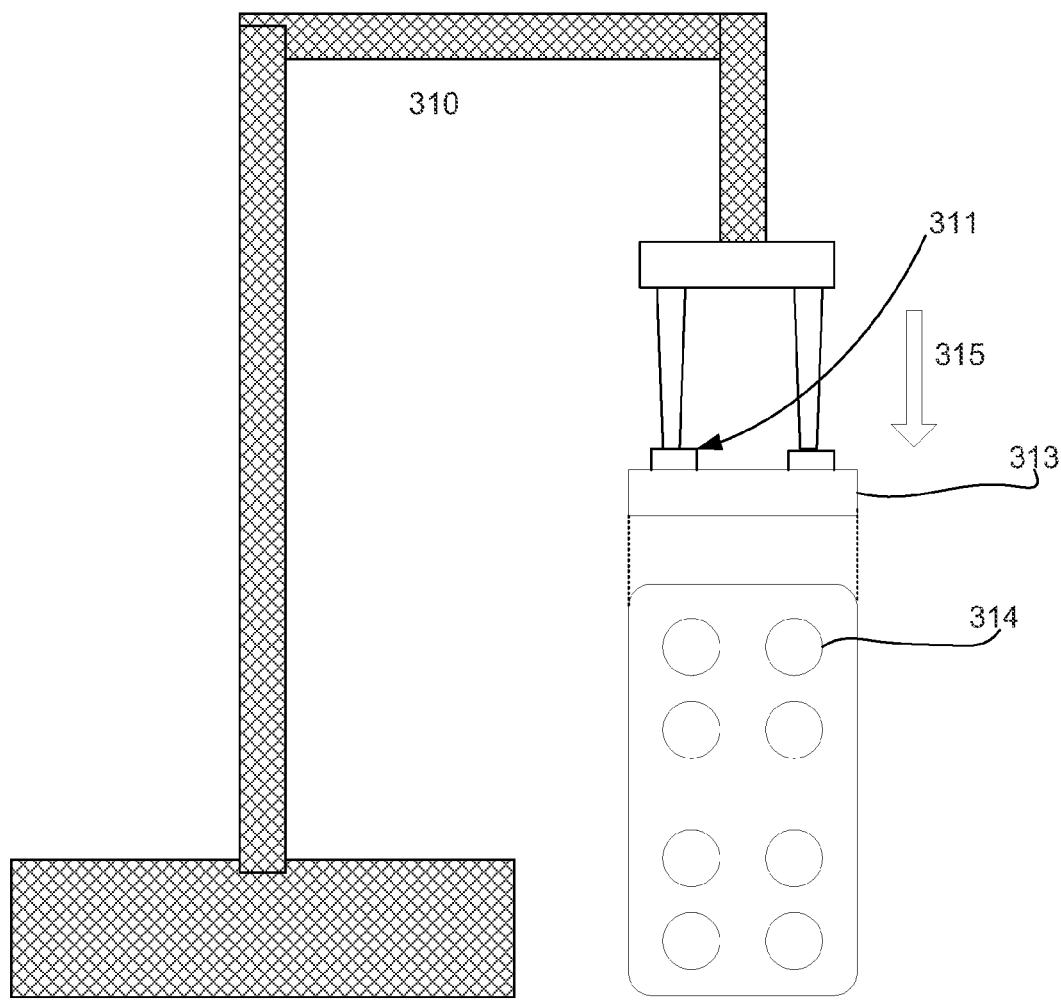
FIG. 3 illustrates an apparatus for placing an Energy Source in proximity to a mold part for forming an ophthalmic lens.

Referring now to FIG. 3, automated apparatus 310 is illustrated with one or more media transfer interfaces 311. As illustrated, multiple mold parts, each with an associated media 314 are contained on a pallet 313 and presented to a media transfer interfaces 311. Embodiments can include a single interface 311 individually placing an Energy Source and a Light Source in multiple media 314, or multiple interfaces (not shown) simultaneously placing Energy Sources and Light Sources in multiple media, such as mold parts 314, and in some embodiments, in each mold.

Another aspect of some embodiments includes apparatus to support the various components comprising an ophthalmic lens Energy Source and Light Source while the body of the ophthalmic lens is molded around these components. In some embodiments the Energy Source and Light Source may affixed to holding points in a lens mold (not illustrated). The holding points may be affixed with polymerized material of the same type that will be formed into the lens body.

Figure 6:
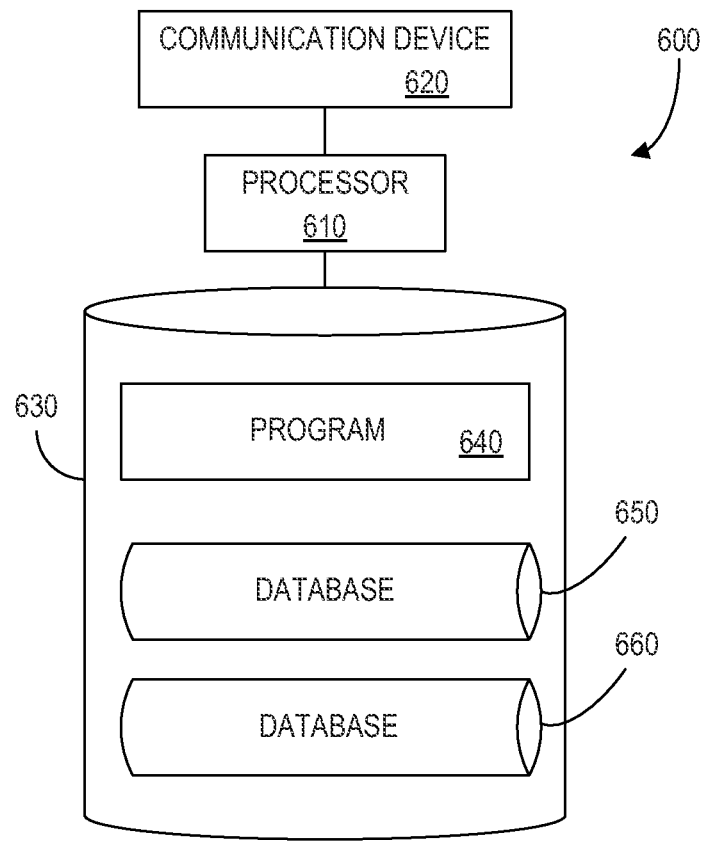
FIG. 6 illustrates a processor that may be used to implement some embodiments of the present invention.

Referring now to FIG. 6 a controller 600 is illustrated that may be used in some embodiments of the present invention. The controller 600 includes a processor 610, which may include one or more processor components coupled to a communication device 620. In some embodiments, a controller 600 can be used to transmit energy to an Energy Source and Light Source placed in an ophthalmic lens.

The controller can include one or more processors, coupled to a communication device configured to communicate energy via a communication channel. The communication device may be used to electronically control one or more of: the placement of an Energy Source into the ophthalmic lens and the transfer of digital data to and from an ophthalmic lens or control of a Light Source or other component incorporated into the ophthalmic lens.

The communication device 620 may also be used to communicate, for example, with one or more controller apparatus or manufacturing equipment components.

The processor 610 is also in communication with a storage device 630. The storage device 630 may comprise any appropriate information storage device, including combinations of magnetic storage devices (e.g., magnetic tape and hard disk drives), optical storage devices, and/or semiconductor memory devices such as Random Access Memory (RAM) devices and Read Only Memory (ROM) devices.

The storage device 630 can store a program 640 for controlling the processor 610. The processor 610 performs instructions of the program 640, and thereby operates in accordance with the present invention. The storage device 630 can also store ophthalmic related data in one or more databases. The database may include customized Energy Source and Light Source designs, metrology data, and specific control sequences for controlling energy to and from an Energy Source and a Light Source.

In some embodiments, an ophthalmic lens with an activation component operative to provide energy from an Energy Source incorporated into an ophthalmic device.

Figure 7:
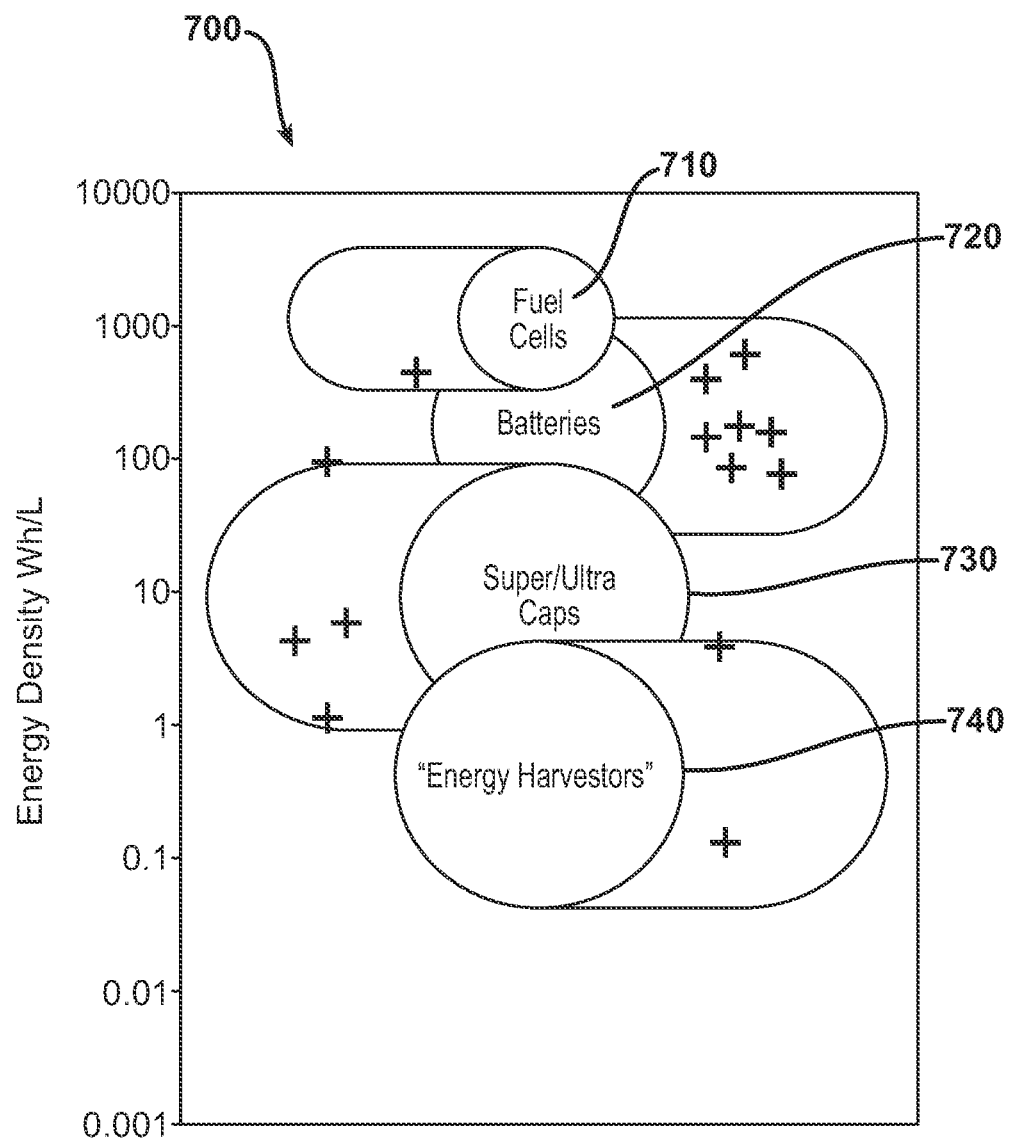
FIG. 7 illustrates a depiction of some exemplary types of energy sources ordered by estimates of the amount of energy that they may provide in ratio to their volume.
Figure 8A:
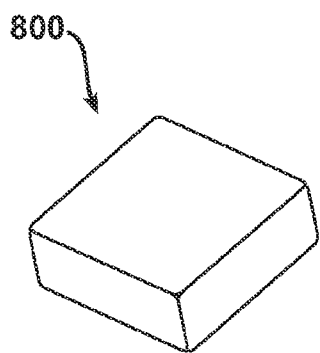
FIGS. 8a-8d illustrate exemplary design shapes for energy sources.
Figure 8B:
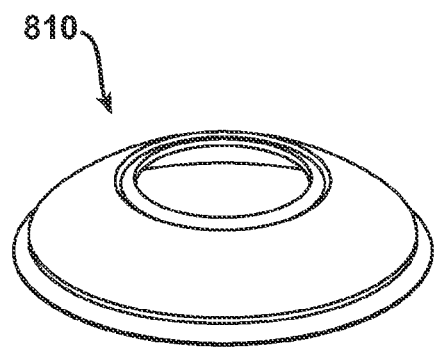
Figure 8C:
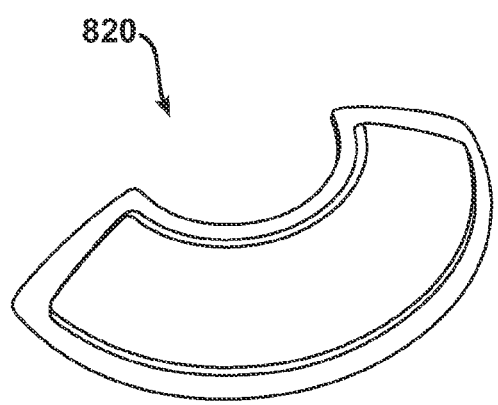
Figure 8D:
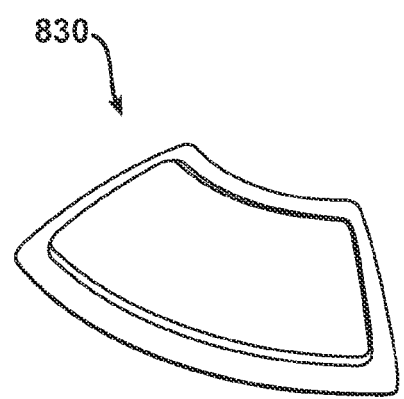

Referring now to FIG. 7, a view of some of the options that may be included in different types of Energy Sources that may be embedded in an energized ophthalmic lens 100 is demonstrated in FIG. 7 as item 700. As previously mentioned, a set of embodiments of Energy Sources can include batteries. Batteries are demonstrated in FIG. 7 as item 720. FIG. 7 also demonstrates a graph of the various options in order of the density of the energy that they can store. Batteries, for example, include a region of energy density from ~50 to ~800 Whr/L. In general, without considering other aspects of a particular Energy Source, the higher density of energy storage the more desirable the source would be.

On this graph 700 it can be seen that energy harvesters, item 740, would be the least desirable from an energy density perspective. However, it may be apparent to one skilled in the art that there are other manners that energy harvesters would have an advantage in.

For example, energy harvesters can include photovoltaic energy cells, thermoelectric cells or piezoelectric cells. Such harvesters have a positive aspect in that they can absorb energy from the environment and then can provide electrical energy without a wired connection. In some embodiments, harvesters may comprise the source in an energized ophthalmic lens. In other embodiments, however, the energy harvester may be combined with other sources that can store energy in an electrical form.

Other types of Energy Source include capacitor type devices 730. It may be apparent, that capacitors comprise an energy density solution that is higher than energy harvesters but less than that of batteries 720. Capacitors, nevertheless, have some inherent advantages.

Capacitors are a type of Energy Source that stores the energy in an electrical form; and therefore, may be one of the Energy Sources that could be combined with energy harvesters to create a wireless Energy Source that is capable of storage of energy. Generally capacitors have an advantage over batteries in that they have higher power density, in general, than batteries. There are many different types of capacitors ranging from standard electrical thin film capacitors, Mylar capacitors, electrolytic capacitors and relative newer and more advanced technologies of high density nanoscale capacitors or supercapacitors.

In some additional embodiments, Energy Sources including electrochemical cells or batteries 720 may define a relatively desirable operational point. Batteries have numerous advantageous characteristics. For example, Batteries store energy in a form that is directly converted to electrical energy. Some batteries may be rechargeable or Re-energizable and therefore, represent another category of Energy Source that may be coupled to energy harvesters. With batteries relatively high energy density, the energy the batteries store can perform functions with reasonable energy requirements. In addition, the batteries can be assembled into forms that are flexible. For applications requiring high power capabilities, it may be apparent to one skilled in the art that a Battery may also be coupled to Capacitors. There may be numerous embodiments that comprise a battery at least as part of an Energy Source in an energized ophthalmic lens.

Another type of embodiment can include a fuel cell as an Energy Source 710. Fuel cells generate electricity by consuming a chemical fuel source which then generates electricity and byproducts including heat energy. Fuel cell embodiments may be possible using biologically available materials as the fuel source. In general, however except for the favorable energy density afforded by this Energy Source, it may suffer from being technologically complex and may typically not be of the necessary small scale required of an ophthalmic application. As well, if the fuel source may not in some manner be extracted from the ophthalmic environment, it may suffer from a practical energy density when compared with an Energy Source that can be reenergized.

The following discussions of the embodiments of this invention may focus generally on using a battery as the principle Energy Source of an energized ophthalmic lens. This focus should not limit the scope of the inventive art, as numerous Energy Sources including those that have been discussed may comprise embodiments of an energized ophthalmic lens.

As mentioned in some embodiments of the present invention the Energy Source includes an electrochemical cell or battery. There are many different types of batteries which may be included in embodiments of energized ophthalmic lenses. For example, single use batteries may be formed from various cathode and anode materials. By way of non-limiting examples these materials may include Zinc, carbon, Silver, Manganese, Cobalt, Lithium, Silicon. Still other embodiments may derive from the use of batteries that are rechargeable. Such batteries may in turn be made of one or more of: Lithium Ion technology; Silver Technology; Magnesium technology; Niobium technology or other current providing material. It may be apparent to one skilled in the art that various current battery technologies for single use or rechargeable battery systems may comprise the Energy Source in various embodiments of an energized ophthalmic lens.

The physical and dimensional constraints of a contact lens environment may favor certain battery types over others. An example of such favorability may occur for thin film batteries. Thin film batteries may occupy the small volume of space consistent with human ophthalmic embodiments. Furthermore, they may be formed upon a substrate that is flexible allowing for the body of both the ophthalmic lens and included battery with substrate to have freedom to flex.

In the case of thin film batteries, examples may include single charge and rechargeable forms. Rechargeable batteries afford the ability of extended usable product lifetime and, therefore, higher energy consumption rates. Much development activity has focused on the technology to produce electrically energized ophthalmic lenses with rechargeable thin film batteries; however, the inventive art is not limited to this subclass.

Rechargeable thin film batteries are commercially available, for example, Oak Ridge National Laboratory has produced various forms since the early 1990s. Current commercial producers of such batteries include Excellatron Solid State, LLC (Atlanta, Ga.), Infinite Power Solutions (Littleton, Colo.), and Cymbet Corporation, (Elk River, Minn.). The technology is currently dominated by uses that include flat thin film batteries. Use of such batteries may comprise some embodiments of this inventive art; however, forming the thin film battery into a three dimensional shape, for example with a spherical radius of curvature comprises desirable embodiments of the inventive art. It may be clear to one skilled in the art that numerous shapes and forms of such a three dimensional battery embodiment are within the scope of the invention.

In FIGS. 8a, 8b, 8c and 8d are numerous examples of different shapes that an Energy Source in an ophthalmic lens may take. Item 800 shows a reference Energy Source made of thin film materials, which for reference is formed as a flat shape. When the dimension of such a shape 800 is of the rough order of a millimeter, it may comprise an Energy Source for an energized ophthalmic lens. Item 810 shows an exemplary 3 dimensional form where the flexible substrate and encapsulated battery assume a full annular shape, which when not flexibly distorted is roughly the same shape that an undistorted ophthalmic lens may assume. In some embodiments, the radius of the annular shape may approximate 8 millimeters for an energized ophthalmic lens embodiment. The same three-dimensional aspect may be shared by embodiments which are quarter annulus 830, or half annulus 820. It may be apparent to one skilled in the arts that many different shapes including other partial annular shapes may comprise alternative embodiments within the scope of this invention.

Another set of embodiments of the present invention relate to the specific battery chemistries which may be advantageously utilized in an energized ophthalmic lens. An example embodiment, which was developed by Oak Ridge Laboratories, comprises constituents of a Lithium or Lithium-Ion Cell. Common materials for the anode of such cells could include Lithium metal or alternatively for the Lithium Ion Cell could include graphite. An example alternative embodiment of these cells would be the incorporation of micro-scaled silicon features to act as the anode of such a thin film battery incorporated into a contact lens.

The materials used for the cathode of the batteries used in this novel art could as well include multiple materials options. Common cathode materials would include Lithium Manganese Oxide and Lithium Cobalt Oxide which have good performance metrics for the batteries thus formed. Alternatively, Lithium Iron Phosphate cathodes, can have similar performance, however, may in some applications have improved aspects relating to charging. As well, the dimension of these and other cathode materials can improve charging performance; as for example, forming the cathode from nano-scaled crystals of the various materials can dramatically improve the rate that the battery may be recharged at.

Some embodiments can include encapsulating the Energy Source and Light Source with a material isolating the Energy Source and Light Source from an environment into which they are placed. It may be desirable to encapsulate the Energy Source and Light Source to generally isolate its constituents from entering the ophthalmic environment. Alternatively, aspects of the ophthalmic environment may negatively affect the performance of Energy Sources and Light Sources if they are not properly isolated by an encapsulation embodiment. Various embodiments of the inventive art may derive from the choice of materials.

Figure 9:
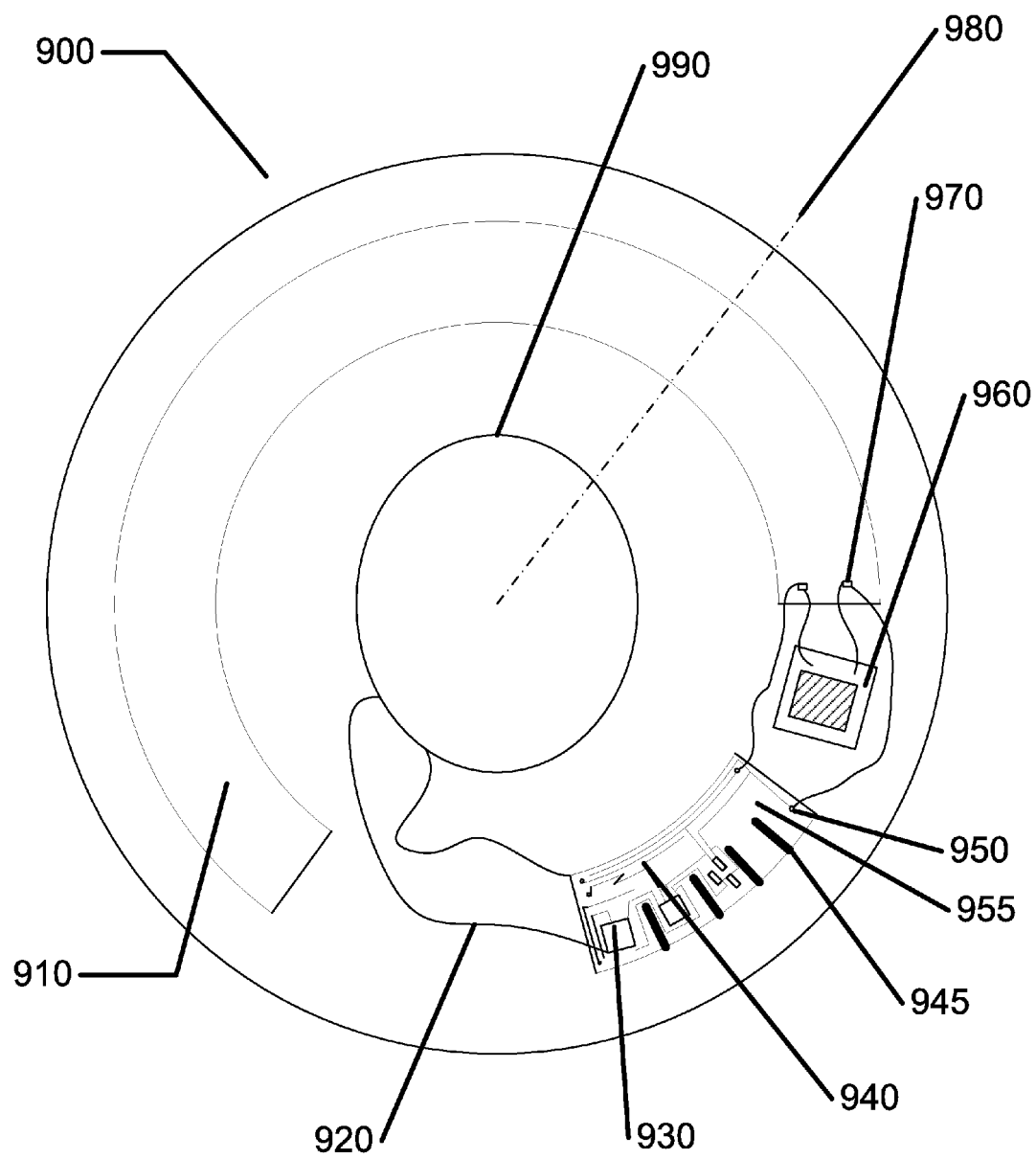
FIG. 9 illustrates an example of an energized ophthalmic lens with a device for reenergization and an energized component.

Referring to FIG. 9, item 900 a depiction of an exemplary embodiment of an energized ophthalmic lens is shown. In this depiction, the Energy Source 910 may include a thin film, rechargeable lithium ion battery. The battery may have contact points 970 to allow for interconnection. Wires may be wire bond wires to the contact points 970 and connect the battery to a photoelectric cell 960 which may be used to reenergize the battery Energy Source 910. Additional wires may connect the Energy Source to a flexible circuit interconnect via wire bonded contacts on a second set of contact points 950. These contact points 950 may be a portion of a flexible interconnect substrate 955 which may also include a Light Source 930. This interconnect substrate may be formed into a shape approximating a typical lens form in a similar manner to the Energy Source previously discussed. However to add additional flexibility, the interconnect substrate 955 may include additional shape features such as radial cuts 945 along its length. On individual flaps of the interconnect substrate 955 may be connected various electronic components like ICs, discrete components, passive components and such devices which are shown as item 990. These components are interconnected by wires or other connection means 940 to the conduction paths within the interconnect substrate 955. By way of non-limiting example, the various components may be connected to the flexible interconnect substrate 955 by the various means that interconnections to the battery already discussed may be made. The combination of the various electrical components may define a control signal for an electro-optical device shown as item 990. This control signal may be conducted along interconnect 920. This type of exemplary energized ophthalmic lens with energized function is provided only for the purpose of example. In no way should this description be construed to limit the scope of the inventive art as it may be apparent to one skilled in the arts that many different embodiments of function, design, interconnection scheme, energization scheme and overall utilization of the concepts of this invention may exist.

In some embodiments there may be manners of affecting the ophthalmic lens' appearance. Aesthetics of the thin film microbattery surface may be altered in various manners which demonstrate a particular appearance when embedded in the electroactive contact lens or shaped hydrogel article. In some embodiments the thin film microbattery may be produced with aesthetically pleasing patterned and/or colored packaging materials which could serve to either give a muted appearance of the thin film microbattery or alternatively provide iris-like colored patterns, solid and/or mixed color patterns, reflective designs, iridescent designs, metallic designs, or potentially any other artistic design or pattern. In other embodiments, the thin film battery may be partially obscured by other components within the lens, for example a photovoltaic chip mounted to the battery anterior surface, or alternatively placement of the battery behind all or a portion of a flexible circuit. In further embodiments, the thin film battery may be strategically located such that either the upper or lower eyelid partially or wholly obscures the visibility of the battery. It may be apparent to one skilled in the art that there are numerous embodiments relating to appearance of an energized ophthalmic device and the methods to define them.

There may be numerous embodiments relating to the method of forming an energized ophthalmic device of the various types that have been described. In one set of embodiments, the inventive art herein may include assembling subcomponents of a particular energized ophthalmic lens embodiment in separate steps. The "off-line" assembly of advantageously shaped thin film microbatteries, flexible circuits, interconnects, microelectronic components, and/or other electroactive components in conjunction with a biocompatible, inert, conformal coating provides an all-inclusive, embeddable singular package that can be simply incorporated into standard contact lens manufacturing processes. Flexible circuits may include those fabricated from copper clad polyimide film or other similar substrates. Conformal coatings may include, but are not limited to, parylene (grades N, C, D, HT, and any combinations thereof), poly (p-xylylene), dielectric coatings, silicone conformal coatings, or any other advantageous biocompatible coatings.

Some embodiments of the present invention may be methods that are directed toward the geometric design of thin film microbatteries in geometries amenable to the embedment within and/or encapsulation by ophthalmic lens materials. Other embodiments may involve methods that incorporate thin film microbatteries in various materials such as, but not limited to, hydrogels, silicone hydrogels, rigid gas-permeable "RGP" contact lens materials, silicones, thermoplastic polymers, thermoplastic elastomers, thermosetting polymers, conformal dielectric/insulating coatings, and hermetic barrier coatings.

Other embodiments may involve methods for the strategic placement of an Energy Source and a Light Source within an ophthalmic lens geometry. Specifically, in some embodiments the Energy Source and Light Source may be opaque articles. Since the Energy Source and Light Source may not obstruct the transmission of light through the ophthalmic lens, methods of design in some embodiments may ensure that the central 5-8 mm of the contact lens may not be obstructed by any opaque portions of the Energy Source and Light Source. It may be apparent to one skilled in the art that there may be many different embodiments relating to the design of various Energy Sources and Light Sources to interact favorably with the optically relevant portions of the ophthalmic lens.

In some embodiments the mass and density of the Energy Source may facilitate designs such that said Energy Source may also function either alone or in conjunction with other lens stabilization zones designed into the body of the ophthalmic lens to rotationally stabilize the lens while on an eye. Such embodiments could be advantageous for a number of applications including, but not limited to, correction of astigmatism, improved on-eye comfort, or consistent/controlled location of other components within the energized ophthalmic lens.

In additional embodiments, the Energy Source and Light Source may be placed a certain distance from the outer edge of the contact lens to enable advantageous design of the contact lens edge profile in order to provide good comfort while minimizing occurrence of adverse events. Examples of such adverse events to be avoided may include superior epithelial arcuate lesions or giant papillary conjunctivitis.

By way of non-limiting example in some embodiments, a cathode, electrolyte and anode features of embedded electrochemical cells may be formed by printing appropriate inks in shapes to define such cathode, electrolyte and anode regions. It may be apparent that batteries thus formed could include both single use cells, based for example on manganese oxide and zinc chemistries, and rechargeable thin batteries based on lithium chemistry similar to the above mentioned thin film battery chemistry. It may be apparent to one skilled in the arts that a variety of different embodiments of the various features and methods of forming energized ophthalmic lenses may involve the use of printing techniques.

Figure 10:
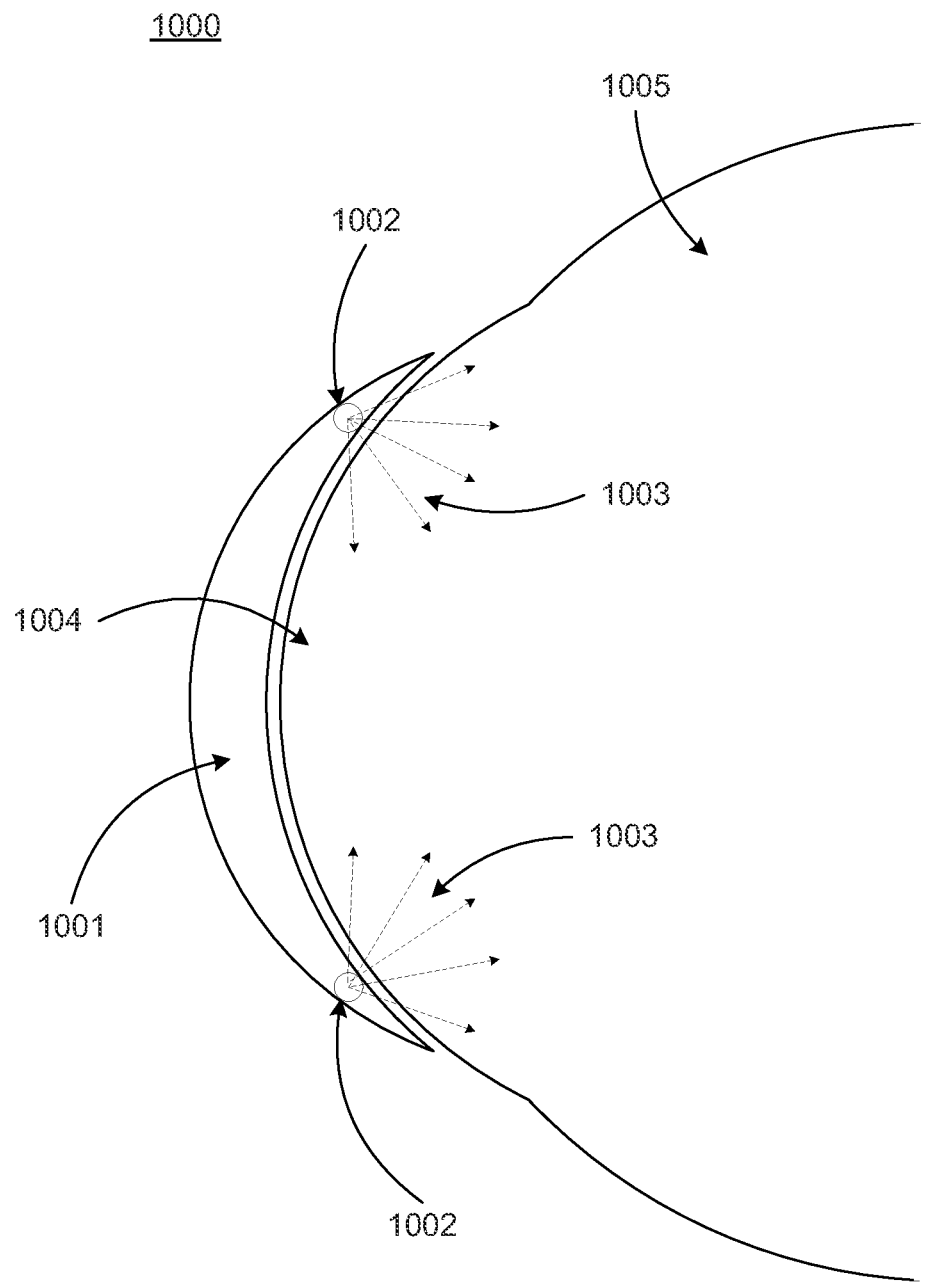
FIG. 10 illustrates a cross-section view of an energized ophthalmic lens containing light sources according to some embodiments of the present invention.

Referring now to FIG. 10, a cross-section view 1000 includes an energized ophthalmic lens 1001, also referred to as a contact lens 1001, with embedded Light Sources 1002 directing light 1003 onto a cornea 1004 of an eye 1005. In some embodiments, a cross-section view 1000 may be a top-down view, wherein one or more embedded Light Sources 1002 are placed near the sides of a contact lens 1001. In other embodiments, a cross-section view 1000 may be a side view, such that one or more embedded Light Sources 1002 are placed near the top and bottom of a contact lens 1001. A number of Light Sources 1002 and an arrangement of Light Sources 1002 around a perimeter of a contact lens 1001 may vary. A Light Source 1002 directs illumination toward a wearer's eye such that illumination is not obvious to an observer. A contact lens 1001 may also include a coating which shields light therapy luminescence from being readily noticed by an observer while not diminishing a user's light therapy or vision.

Embedded Light Sources 1002 include light-emitting diodes (LEDs) or other Light Sources 1002 emitting light 1003 for light therapy. Light Sources 1002 may include light-emitting diodes (LEDs) or other lights which emit blue light at wavelengths of 450 to 500 nanometers, most preferably at 470 to 480 nanometers, and at 2,000 to 3,000 lux. Alternatively, LEDs or other lights may emit green light at wavelengths of 475 to 525 nanometers, most preferably at 490 to 510 nanometers, and at 300 to 400 lux. Another embodiment includes a single Light Source from which light is piped to one or more locations within a contact lens 1001 to provide illumination.

A contact lens 1001 includes supporting electronics, not illustrated, with components such as, for example, light sensors, Energy Source, capacitors, memory, processor, and communication device. Light sensors are used to detect ambient white light, blue light or green light. An Energy Source and capacitors supply energy to other components of an energized ophthalmic lens. Memory may be used, by way of non-limiting example, to store pre-programmed light therapy schedules, to store data captured by light sensors, to store actual light therapy dates, times, durations and intensities, and to store data related to light source and light sensor operation in order to detect device failures. A processor may be used, for example, to run programmed light therapy schedules stored in memory, to analyze light sensor data and determine a unique light therapy schedule based on the wearer's exposure to ambient light, to evaluate manual changes to a programmed light therapy schedule and provide compensating adjustments, and to analyze light source and light sensor data to detect device failures.

A communication device may be used to electronically control one or more of: the transfer of digital data to and from an energized ophthalmic lens and external devices, and the transfer of digital data between components within the energized ophthalmic lens. The communication device may be used to wirelessly communicate with one or more external devices, such as by way of non-limiting example, a fob, a personal digital assistant (PDA), or a Smartphone application used to control an energized ophthalmic lens. Within an energized ophthalmic lens, communication between components may be via physical connection, such as via a direct conductive path, or may be wireless. Communication between internal components may include, for example, control of a Light Source from a processor and data transfer between light sensors and memory.

Supporting electronics are in logical and electrical communication with Light Sources 1002 contained within a contact lens 1001. Communication may be via a direct conductive path between supporting electronics and Light Sources 1002 or via wireless communication. Wireless modes of communication may include, for example, inductance accomplished via an antenna located proximate to a Light Source 1002 in a contact lens 1001 and a power source transmitting power from another area within a contact lens 1001 to the antenna.

In some embodiments, supporting electronics may be included in a fob, jewelry, hat, clothing, or other items worn by a user such that light sensors detect ambient light experienced by the user and supporting electronics are near a contact lens for purposes of wireless communication. Wireless modes of communication may include, for example, inductance. Inductance may be accomplished via an antenna located in a contact lens and a power source transmitting power from supporting electronics in jewelry, clothing, or other item proximate to the antenna.

In some embodiments, a user may adjust timing, duration and intensity of light therapy using an external device, such as a fob, a personal digital assistant, or a Smartphone application. Some embodiments provide for a basic operational state, wherein light therapy is controlled manually by a user starting and stopping therapy at appropriate times.

According to the present embodiment, a programmed light therapy schedule may, for example, automatically adjust light therapy timing, duration and intensity based on variables such as dates, geographic region, and severity of a user's seasonal affective disorder symptoms. A programmed light therapy schedule may be set by an eye care professional, a medical doctor, or a user. During programmed light therapy, it may be desirable for a user to adjust light intensity based on an activity, such as, for example, decreasing light intensity when reading, working on a computer, or driving. Conversely, it may be desirable to increase light intensity during work breaks, lunch break, or other less visually active times. In some embodiments, intelligent light therapy is delivered when a processor evaluates manual changes to a programmed light therapy schedule and provides compensating adjustments in duration and intensity of treatment. In still other embodiments, intelligent light therapy is achieved when data from light sensors is analyzed by a processor and a programmed light therapy schedule is dynamically adjusted based on a wearer's exposure to ambient light.

In another embodiment of the present invention, a user may manually adjust light therapy based on the results of blood testing for melatonin levels. Melatonin produced by the pineal gland is inhibited by light and increases with darkness. Higher levels of melatonin promote sleepiness and lethargy, symptoms of seasonal affective disorder. Analysis of the level of melatonin in a patient's blood may be used as a guide to increase or decrease light therapy.

In still other embodiments, a user may manually adjust light therapy to intentionally alter their sleep cycle. The use of light therapy for sleep cycle alteration may be valuable for persons working night shifts, for persons travelling to significantly different time zones, for military personnel preparing for night operations, and other uses. Additionally, light therapy initiated by the user upon awakening may be used to treat circadian rhythm disorders such as delayed sleep phase syndrome (DSPS) and non-24-hour sleep-wake syndrome.

In some embodiments, a Light Source 1002 may direct light 1003 into an interior portion of a contact lens 1001 in which the Light Source 1002 is embedded. Light 1003 may be directed into a light scattering area, not depicted, including diffractive properties, refractive properties, reflective properties, or any combination of diffractive, refractive and reflective properties. A light scattering area may form an annulus within a perimeter area of a contact lens 1001. Light 1003 striking a light scattering area causes a generally broad dispersion of light 1003 onto a cornea 1004 of an eye 1005.

In some preferred embodiments, a contact lens 1001 may include an internal barrier between a light scattering area around a perimeter of a lens and an optical zone in a central portion of a lens. An internal barrier prevents light 1003 intended for light therapy from being dispersed into an optical zone of a contact lens 1001. In this way, light 1003 intended for light therapy is only dispersed around a perimeter of a cornea 1004, minimizing its effect on normal vision.

In still other embodiments, an entire contact lens 1001 includes light scattering properties such as diffraction, refraction or reflection. Light scattering properties are designed such that they disperse only light 1003 of wavelengths emitted by embedded Light Sources 1002. This embodiment supports maximum dispersion of light 1003 wavelengths intended for light therapy within an eye 1005 while not causing dispersion of light wavelengths that would distort vision.

Conclusion

The present invention, as described above and as further defined by the claims below, provides methods of processing ophthalmic lenses with light sources for delivering light therapy and apparatus for implementing such methods, as well as ophthalmic lenses formed thereby.

What is claimed is:

1. A method of forming an ophthalmic lens, the method comprising:
   placing an energy source in electrical communication with a light source proximate to a first mold part;
   depositing a reactive monomer mix into the first mold part;
   positioning the energy source and light source in contact with the reactive monomer mix;
   positioning the first mold part proximate to a second mold part thereby forming a lens cavity with the energy source and light source and at least some of the reactive monomer mix in the lens cavity; and
   exposing the reactive monomer mix to actinic radiation.

2. The method of claim 1 wherein the energy source comprises an electrochemical cell.

3. The method of claim 2 wherein the energy source is capable of providing power to the light source to emit light from the light source.

4. The method of claim 2 wherein the energy source is physically attached to a substrate and the substrate is placed in contact with one or both of the first mold part and the second mold part.

5. The method of claim 4 wherein the substrate comprises an integrated circuit and the method additionally comprises the step of fixing the energy source to the substrate.

6. The method of claim 5 wherein the substrate comprises multiple disparate portions.

7. The method of claim 1 wherein the energy source comprises a thin film electrochemical cell.

8. The method of claim 7 wherein the electrochemical cell comprises a lithium ion battery.

9. The method of claim 7 wherein the electrochemical cell comprises a rechargeable solid state material.

10. The method of claim 7 wherein the electrochemical cell comprises a cathode comprising nano-scaled crystals.

11. The method of claim 10 wherein the nano-scaled crystals comprise lithium iron phosphide.

12. The method of claim 1 wherein the light source emits blue light at wavelengths of 450 to 500 nanometers.

13. The method of claim 12 wherein the light source emits blue light at wavelengths of 470 to 480 nanometers.

14. The method of claim 13 wherein the light source emits between about 2,000 to 3,000 lux of light.

15. The method of claim 1 wherein the light source emits green light at wavelengths of 475 to 525 nanometers.

16. The method of claim 15 wherein the light source emits green light at wavelengths of 490 to 510 nanometers.

17. The method of claim 16 wherein the light emits between about 300 to 400 lux of light.

18. The method of claim 1 wherein the light source comprises one or more light emitting diodes.

19. The method of claim 18 wherein the light source comprises one or more light pipes.

20. The method of claim 19 wherein the one or more light pipes comprise fiber optic pathways.

21. The method of claim 1, wherein the ophthalmic lens includes an annular area including a light scattering area around a periphery of an optic zone and the energy source and the light source are positioned within the annular area.

22. The method of claim 21, wherein the central 5 mm of the ophthalmic lens is not obstructed by any opaque portion of the energy source and light source.

23. The method of claim 21, wherein the light source is positioned to direct illumination toward a wearer's eye.

24. The method of claim 23, wherein the light scattering area causes a generally broad dispersion of light from the light source onto the cornea of an eye.

25. The method of claim 24, wherein the light scattering area forms an annulus within a perimeter area of the ophthalmic lens.

26. The method of claim 21, wherein the ophthalmic lens includes an internal barrier between the light scattering area and the perimeter of the optic zone of the lens.

27. The method of claim 21, further comprises placing a memory storage device and a processor proximate to said first mold part.

28. The method of claim 27, wherein the processor is capable of determining a schedule for operating the light source.

* * * * *